United States Patent [19]

Kise et al.

[11] Patent Number: 5,086,049
[45] Date of Patent: Feb. 4, 1992

[54] 7[4-(5 METHYL-2-OXO-1,3-DIOXALEN-4-YL)METHYL 1-PIPERZINYL]-4-OXO-4H-[1,3]THIAZETO[3,2-A]QUINOLINE-3-CARBOXYLIC ACIDS

[75] Inventors: Masahiro Kise; Masahiko Kitano, both of Kyoto; Masakuni Ozaki, Joyo; Kenji Kazuno, Rittocho; Masahito Matsuda, Otsu; Ichiro Shirahase; Jun Segawa, both of Kyoto, all of Japan

[73] Assignee: Nipponshinyaku Co., Ltd., Japan

[21] Appl. No.: 682,434

[22] Filed: Apr. 8, 1991

Related U.S. Application Data

[63] Continuation of Ser. No. 267,940, Nov. 7, 1988, abandoned.

[30] Foreign Application Priority Data

Nov. 7, 1987 [JP] Japan .................. 62-281550

[51] Int. Cl.$^5$ ............. A61K 31/47; C07D 513/04
[52] U.S. Cl. ................... 514/210; 514/254; 544/361
[58] Field of Search ............ 544/361; 514/254

[56] References Cited

U.S. PATENT DOCUMENTS

| | | | |
|---|---|---|---|
| 4,455,310 | 6/1984 | Sakamoto et al. | 514/254 |
| 4,659,734 | 4/1987 | Enomoto | 514/255 |
| 4,703,047 | 10/1987 | Petersen et al. | 514/254 |
| 4,806,539 | 2/1989 | Petersen et al. | 544/379 |
| 4,843,070 | 6/1989 | Kise et al. | 544/361 |
| 4,882,328 | 11/1989 | Kise et al. | 544/361 |
| 5,011,831 | 4/1991 | Kise et al. | 544/361 |

FOREIGN PATENT DOCUMENTS

| | | | |
|---|---|---|---|
| 51-203067 | 12/1982 | Japan . | |
| 0227887 | 12/1984 | Japan | 514/254 |

OTHER PUBLICATIONS

Derwent Abstract of Japan 0227887.

*Primary Examiner*—Donald G. Daus
*Attorney, Agent, or Firm*—Roseman & Colin

[57] ABSTRACT

Quinolinecarboxylic acid derivatives of the formula (I)

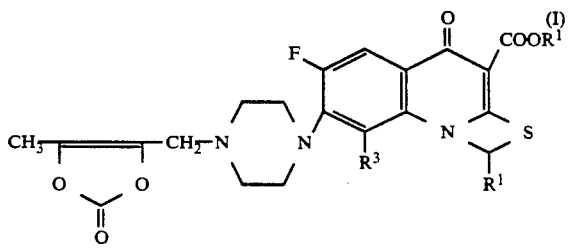

and pharmaceutically acceptable salts thereof, wherein $R^1$ is hydrogen, straight or branch chain lower alkyl or phenyl unsubstituted or substituted by one or more halo moieties; $R^2$ is hydrogen or straight or branch chain lower alkyl; and $R^3$ is hydrogen, halo or straight or branch chain lower alkoxy, are useful for treating bacterial infections in humans and animals.

24 Claims, No Drawings

7[4-(5 METHYL-2-OXO-1,3-DIOXALEN-4-YL)METHYL 1-PIPERZINYL]-4-OXO-4H-[1,3]THIAZETO[3,2-A]QUINOLINE-3-CARBOXYLIC ACIDS

This is a continuation of Ser. No. 267,940 filed Nov. 7 1988, now abandoned.

The present invention is concerned with quinolinecarboxylic acid derivatives and pharmaceutically acceptable salts thereof which are useful for treating bacterial infections in humans and animals.

Nalidixic acid, piromidic acid, pipemidic acid, enoxacin (AT-2266), ofloxacin (DL-8280), and the like are known in the art and have been widely used as synthetic antibacterial agents for the treatment of gram-negative bacteria infections. However, these substances are not satisfactory for the treatment of gram-positive bacterial infections nor are they satisfactory for the treatment of chronic infectious diseases caused by Pseudomonas aeruginosa.

The present inventors have found quinolinecarboxylic acids to have antibacterial activity and have filed a Japanese Patent Application No. 79993/1987 directed thereto. Although these compounds exhibit good antibacterial activity, they have not proved to be fully satisfactory in terms of bioavailability on administration to humans and animals.

One of the objects of the present invention was to develop antibacterial agents having better bioavailability than previously known antibacterial agents.

More particularly, the present invention is concerned with quinolinecarboxylic acid derivatives of the formula (I)

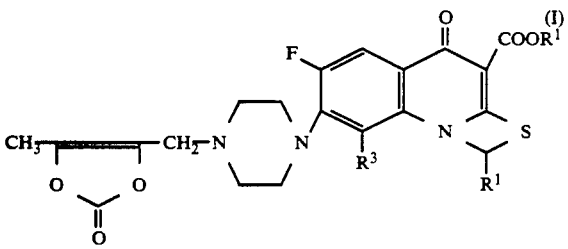

and pharmaceutically acceptable salts thereof wherein $R^1$ is hydrogen, straight or branch chain lower alkyl or phenyl unsubstituted or substituted by one or more halo moieties; $R^2$ is hydrogen or straight or branch chain lower alkyl; and $R^3$ is hydrogen, halo or straight or branch chain lower alkoxy.

These novel compounds of the present invention are characterized by two novel aspects:
1. A ring formed between the nitrogen atom and the sulphur atom in the 2-mercaptoquinolone skeleton is thiazetidine; and
2. The 6- and 7-positions of the quinoline skeleton are substituted with fluorine and with N-(5-methyl-2-oxo-1,3-dioxolen-4-yl)methyl, respectively.

When $R^1$ and/or $R^2$ are alkyl moieties, they are preferably methyl, ethyl, n-propyl, isopropyl, n-butyl, isobutyl, secbutyl or tert-butyl.

When the phenyl moiety of $R^1$ is substituted by halogen, it may be substituted with one or more fluoro, chloro, bromo or iodo moieties. Fluoro substitution is particularly preferred.

When $R^3$ is alkoxy, it is preferably methoxy, ethoxy, n-propoxy, isopropoxy, n-butoxy, isobutoxy, secbutoxy or tert-butoxy.

When $R^3$ is halo, it can be fluoro, chloro, bromo or iodo. Fluoro is particularly preferred.

According to one embodiment of the present invention, $R^1$ is hydrogen, straight or branch chain alkyl of 1 to 4 carbon atoms or phenyl unsubstituted or substituted by one or more halo moieties.

According to another embodiment of the present invention, $R^2$ is hydrogen or straight or branch chain alkyl of 1 to 4 carbon atoms.

According to a further embodiment of the present invention, $R^3$ is hydrogen, halo or straight or branch chain alkoxy of 1 to 4 carbon atoms.

According to a further embodiment of the present invention, $R^1$ is hydrogen, straight or branch chain alkyl of 1 to 4 carbon atoms, phenyl or halophenyl; $R^2$ is hydrogen or straight or branch chain alkyl of 1 to 4 carbon atoms; and $R^3$ is hydrogen, halo or straight or branch chain alkoxy of 1 to 4 carbon atoms.

According to a further embodiment of the present invention, $R^1$ is hydrogen, straight or branch chain alkyl of 1 to 4 carbon atoms, phenyl or fluorophenyl; $R^2$ is hydrogen or straight or branch chain alkyl of 1 to 4 carbon atoms; and $R^3$ is hydrogen, fluoro or straight or branch chain alkoxy of 1 to 4 carbon atoms.

According to a further embodiment of the present invention, the compound of formula (I) is in the form of a pharmaceutically acceptable salt. Suitable salts according to the present invention are salts with mineral acids such as hydrochloric acid, sulfuric acid, nitric acid, phosphoric acid, hydrofluoric acid, hydrobromic acid and the like; salts with organic acids such as formic acid, acetic acid, tartaric acid, lactic acid, citric acid, fumaric acid, maleic acid, succinic acid, methanesulfonic acid, ethanesulfonic acid, benzenesulfonic acid, toluenesulfonic acid, naphthalenesulfonic acid, camphorsulfonic acid and the like; and salts with alkali metals or alkali earth metals such as sodium, potassium, calcium and the like.

Preferred compounds, according to the present invention are those set forth in the examples below.

The compounds of the present invention can be prepared in accordance with the following procedure:

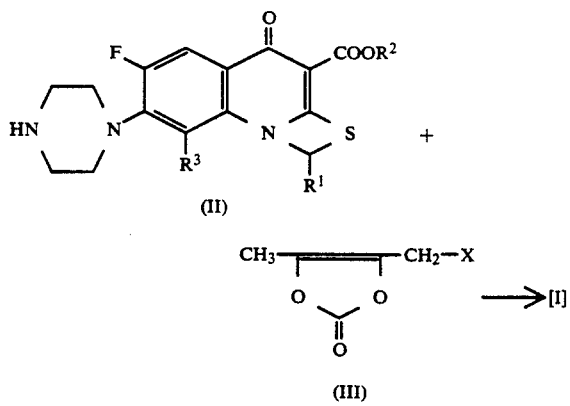

wherein $R^1$, $R^2$ and $R^3$ are as above defined and X is halogen.

The compound of the formula (II) is reacted with the compound of the formula (III) in the presence or absence of a solvent which is inert to the reaction in the presence of a base (e.g. sodium carbonate, potassium carbonate, sodium bicarbonate, potassium bicarbonate, triethylamine, etc.) usually at −20° to +80° C., preferably at −5° C. to room temperature, to afford (I).

Examples of suitable solvents used are preferably aprotic ones such as N,N-dimethylformamide, dimethyl sulfoxide, ethers such as diglyme, etc.

The amount of (III) is preferably equimolar or an excess to one mole of (II). Reaction time may vary depending upon the type and amount of the starting materials, solvents, base, etc. and the reaction temperature but, usually, it is from 2 to 20 hours.

When the compounds prepared in accordance with the above method is an ester ($R^2$ is alkyl), it may, if and when desired, be hydrolyzed to give the corresponding carboxylic acid ($R^2$ is hydrogen). The hydrolysis can be conducted by the use of a great excess of acid (e.g. sulfuric acid, fuming sulfuric acid, hydrochloric acid, hydrobromic acid, hydrobromic acid/acetic acid, chlorosulfonic acid, polyphosphoric acid, etc.), preferably 10 to 20 times as much acid, as a solvent at the temperature of from room temperature to 110° C. Alternatively, the hydrolysis may be conducted by stirring at the temperature of from room temperature to 60° C. in 2 to 30 times as much volume (preferably 5 to 10 times as much volume) of 1 to 5% solution of potassium hydroxide or sodium hydroxide in aqueous alcohol such as methanol, ethanol, propanol or butanol (preferably, tert-butanol).

Further, the ester may be heated at 60°–150° C., preferably at 100°–110° C., with stirring in 10 to 100 times as much amount of alcohol corresponding to the desired ester in the presence of a catalytic amount of concentrated sulfuric acid so that the ester can be converted to desired another ester.

In the case of a carboxylic acid (i.e. $R^2$ is hydrogen), it can, if and when desired, be esterified to give the desired ester (i.e. $R^2$ is alkyl). This esterification reaction can be conducted by a method known per se such as, for example, by the use of thionyl chloride with an alcohol, a condensing agent (e.g. dicyclocarbodiimide) with an alcohol, or an alkyl halide with an alcoholate. Furthermore, in the case of a carboxylic acid, it can be used in a form of a pharmacologically-acceptable salt such as the sodium or potassium salt.

Both starting materials (II) and (III) are known prepared as follows.

When $R^{1'}$, $R^{2'}$ and /or $R^{3'}$ are alkyl, preferred examples are straight or branched chain alkyl having from about 1 to about 6 carbon atoms, such as methyl, ethyl, n-propyl, isopropyl, n-butyl, isobutyl, sec-butyl, tert-butyl, n-pentyl, isopentyl, n-hexyl, isohexyl, and the like.

When $R^{1'}$ is substituted phenyl, it is preferred that $R^{1'}$ is phenyl substituted by alkyl, alkoxy, hydroxy, halogen, trifluoromethyl, nitro, and the like. Preferably an alkyl substituent is straight or branched chain alkyl of from about 1 to about 6 carbon atoms and an alkoxy substituent is straight or branched alkoxy having from about 1 to about 4 carbon atoms, such as methoxy, ethoxy, n-propoxy, isopropoxy, n-butoxy, isobtoxy, sec-butoxy, tert-butoxy, and the like.

When the $R^{1'}$ is phenyl substituted by halogen or $R^{2'}$ is halogen, it is preferred that halogen is chlorine, bromine, iodine, and fluorine, and most preferably fluorine.

When $R^{2'}$ is alkoxy, it is preferred that $R^{2'}$ is alkoxy having from about 1 to about 4 carbon atoms, examples of which are set forth above.

When $R^{2'}$ is substituted amino, it is preferred that $R^{2'}$ is acylamino in which the acyl moiety has from about 2 to about 6 carbon atoms, such as acetylamino, propionylamino, and the like.

When $R^{3'}$ is substituted alkyl, it is preferred that $R^{3'}$ is alkyl substituted by hydroxy, acyloxy of from about 2 to about 6 carbon atoms, such as acetyloxy, propionyloxy, n-butyryloxy, isobutyryloxy, valeryloxy, isovaleryloxy, pivaloyloxy, n-hexanoyloxy, etc. and alkoxy of from about 1 to about 4 carbon atoms, and the like, examples of which are provided above.

When X' is halogen, X' is preferably chlorine, bromine, iodine or fluorine, most preferably fluorine or chlorine.

When $R^{4'}$ or $R^{5'}$ is alkyl or hydroxyalkyl, it is preferred that the alkyl moiety is straight or branched alkyl having from about 1 to about 4 carbon atoms, such as methyl, ethyl, n-propyl, isopropyl, n-butyl, isobutyl, and the like. Pre-ferred hydroxyalkyl includes 2-hydroxyethyl, 3-hydroxypropyl, 2-hydroxypropyl, and the like.

When $R^{4'}$ and $R^{5'}$ form a heterocyclic ring, it is preferred that the heterocyclic ring have from about 4 to about 8 ring members, which may further contain nitrogen, oxygen or sulphur atoms as additional heteroatoms therein. Examples of heterocyclic rings include azetidino, pyrrolidino, piperidino, azepino, azocino, piperazino, homopiperazino, pyrrolino, morpholino, thiomorpholino, imidazolino, imidazolidino, imidazolinino, pyrazolidino, pyrazolino, and the like.

If desired, the heterocyclic ring preferably has from one to three substituents, which may be the same or different. Examples of such substituents include alkyl, alkenyl, alkynyl, aryl, aralkyl, hydroxyalkyl, alkoxyalkyl, aminoalkyl, cyanoalkyl, carboalkoxyalkyl, acylalkyl, acyl, hydroxy, oxo, amino, alkylamino, dialkylamino, and the like. The alkyl substituent may include those exemplified for $R^{1'}$ hereinabove. The alkenyl substituent may be straight or branched alkenyl having from about 2 to about 6 carbon atoms, such as vinyl, allyl, isopropenyl, 2-methallyl, 2-butenyl, 3-butenyl, and the like. Examples of alkynyl include straight or branched alkynyl having from about 2 to about 6 carbon atoms, such as ethynyl, 1-propynyl, and 2-propynyl. Examples of aryl include phenyl, alpha-naphthyl, beta-napthyl, biphenyl, and the like, most preferably phenyl. Examples of aralkyl include aralkyl having from about 7 to about 12 carbon atoms, such as benzyl, phenethyl, phenylpropyl, naphthylmethyl, and the like.

The hydroxyalkyl preferably has from about 1 to about 4 carbon atoms, such as hydroxymethyl, 2-hydroxyethyl, 3-hydroxypropyl, 2-hydroxypropyl, and the like, while alkoxyalkyl having from about 2 to about 6 carbon atoms is preferred, such as, for example, methoxyethyl, ethoxymethyl, and ethoxyethyl. The alkoxyalkyl may also be further substituted with hydroxyl. It is preferred that aminoalkyl has from about 1 to about 4 carbon atoms, such as aminomethyl, 2-aminoethyl, 3-aminopropyl, 4-aminobutyl, and the like. Cyanoalkyl having from about 2 to about 4 carbon atoms is preferred, such as cyanomethyl, 2-cyanoethyl, and 3-cyanopropyl. Carboalkoxyalkyl preferably has 1 to 4 carbon atoms in the alkoxy and alkyl moieties.

Acylalkyl having from about 3 to about 10 carbon atoms is preferred, such as acyl from about 2 to about 6 carbon atoms (as exemplified in the acyloxy for $R^{3'}$) to which alkylene from about 1 to about 4 carbon atoms is combined. Such as acylalkyl may be further substituted with carboxy, carbo-methoxy, carboethoxy, and the like. The acyl substituent preferably has from about 1 to about 6 carbon atoms, such as formyl as exemplified above.

The alkylamino substituent preferably has from about 1 to about 4 carbon atoms, such as methylamino, ethylamino, n-propylamino, isopropylamino, n-butylamino, and the like, and the dialkylamino preferably has from about 1 to about 4 carbon atoms in each alkyl moiety, such as dimethylamino, diethyl-amino, di-(n-propyl)amino and the like.

When any of the above substituents has a benzene ring, the benzene ring may be further substituted with alkoxy of from about 1 to about 4 carbon atoms or amino which is exemplified as hereinabove.

Examples of pharmaceutically acceptable salts of the compound (II) of the present invention are salts with mineral acids such as hydrochloric acid, sulfuric acid, nitric acid, phosphoric acid, hydrofluoric acid, hydrobromic acid, and the like, salts with organic acids such as formic acid, acetic acid, tartaric acid, lactic acid, citric acid, fumaric acid, maleic acid, succinic acid, methanesulfonic acid, ethanesul-fonic acid, benzenesulfonic acid, toluenesulfonic acid, naphthalenesulfonic acid, camphorsulfonic acid, and the like, and salts with alkali metal or alkali earth metals such as sodium, potassium, calcium, and the like.

Compound II of the present invention may, for example, be manufactured by the following methods:

Method A

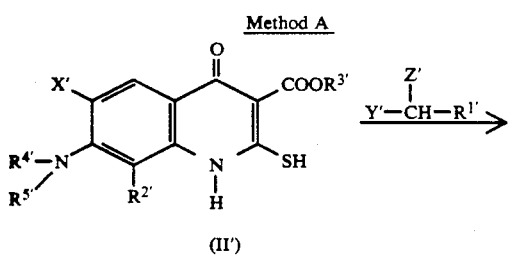

In the formulae, $R^{1'}$, $R^{2'}$, $R^{4'}$, $R^{5'}$ and $X'$ are the same as those already defined; $Y'$ and $Z'$ are same or different halogens; and $R^{3'}$ is alkyl.

Method B

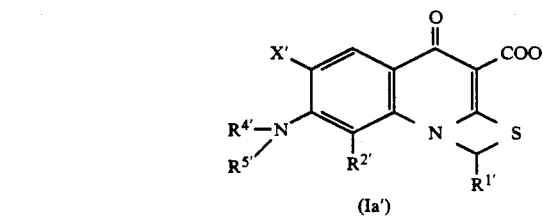

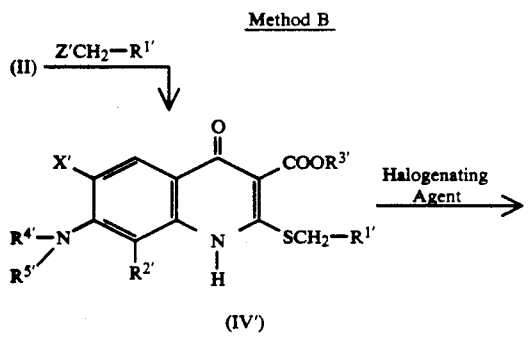

Method B -continued

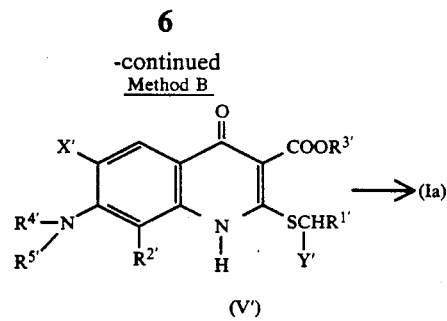

In the formulae, $R^{1'}$, $R^{2'}$, $R^{3'}$, $R^{4'}$, $R^{5'}$, $X'$, $Y'$ and $Z'$ are the same as those in the Method A.

Method C

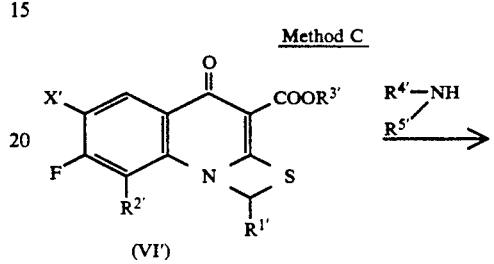

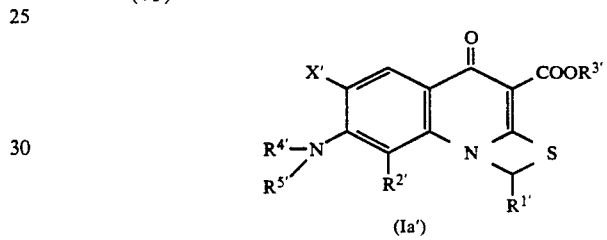

In the formulae, $X'$, $R^{1'}$, $R^{2'}$, $R^{3'}$, $R^{4'}$, and $R^{5'}$ are the same as those in the Method A.

Method D

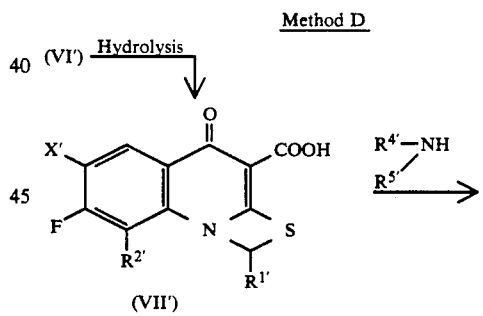

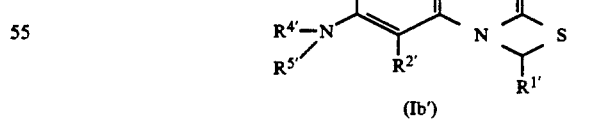

In the formulae $X'$, $R^{1'}$, $R^{2'}$, $R^{4'}$ and $R^{5'}$ are the same as those hereinabove.

It will be apparent from the above description that the compound II of the present invention can be produced by two routes. One is to form a thiazetidine ring using quinolinecarboxylic acid substituted with an amino group at the 7-position of a starting material (Methods A and B) while the other is to form the thiazetidine ring followed by introducing an amino group in the 7-position (Methods C and D). These methods will be described in more detail below.

Method A: (II') and the dihalide, CHY'Z'R¹', (e.g. methylene iodide, ethylidene bromide, benzylidene bromide, and the like) are reacted usually at 0° to 120° C., in the presence of an acid removing agent (e.g. sodium carbonate, potassium carbonate, triethylamine, etc.) in a solvent which is inert to the reaction whereupon cyclization results, giving (IIa'). As to the solvent, nonprotonic solvent such as N,N-dimethylformamide, N,N-dimethylacetamide, dimethyl sulfoxide, sulfolane, and the like is preferred. The amounts of dihalide and acid removing agent are preferably not less than equimolar, and, more preferably 1.1 to 2.5 moles per mole of (II'). In order to accelerate the reaction, the reaction may be conducted by addition of a catalytic amount (0.01 to 0.1 molar equivalent) of sodium iodide or potassium iodide.

Method B: (II') and the halide (Z'CH₂R¹') are generally reacted at 0° to 80° C. using the same solvent and acid removing agent as in Method A to manufacture (IV'). Then (IV') is halogenated with a halogenating agent (e.g. N-bromosuccinic imide, N-chlorosuccinic imide, and the like) in an inert solvent (e.g. chloroform, dichloromethane, carbon tetrachloride or other halogenated hydrocarbon type solvent) to give (V'). Then (V') is cyclized generally at 0° to 80° C. by the use of the same solvent and acid removing agent as in Method A to afford (IIa').

Method C: (VI') is condensed with the amine (NHR⁴'R⁵') to give (IIa'). In this reaction, the amine is reacted in a solvent which is inert to the reaction (e.g. N,N-dimethylformamide, N,N-dimethylacetamide, dimethyl sulfoxide, sulfolane, acetonitrile, or other nonprotonic solvent) usually at 0° to 80° C. (e.g. 40° to 60° C.). The amount of the amine is 1.5 to 2.5 moles per mole of (VI').

Method D: (VI') is hydrolyzed using an acid (e.g. concentrated sulfuric acid, fuming sulfuric acid, polyphosphoric acid or a mixture thereof) to give (VII'). This reaction is conducted using an excess (e.g. 1 to 30 times excess weight and, more preferably, 5 to 10 times excess by weight) of acid as a solvent usually at 0° to 60° C. This hydrolysis reaction may also be conducted in 20 to 30 times excess by weight (preferably 5 to 10 times excess by weight) of 1-5% potassium hydroxide or sodium hydroxide in aqueous alcohol (methanol, ethanol, propanol, butanol, and the like) generally at room temperature to 60° C. Then (VII') is reacted with the amine (NHR⁴'R⁵') in the same solvent as used in Method C to give (IIb'). The reaction is usually conducted at 0° to 60° C. and, more preferably, 0° C. to room temperature.

There are other methods, and one of them is to start from a compound of the general formula (VIII'), whereby the product can be manufactured by the following route:

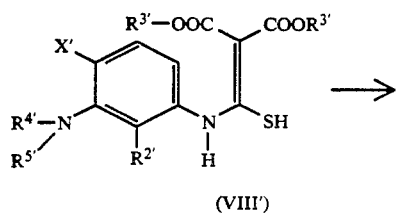

(VIII')

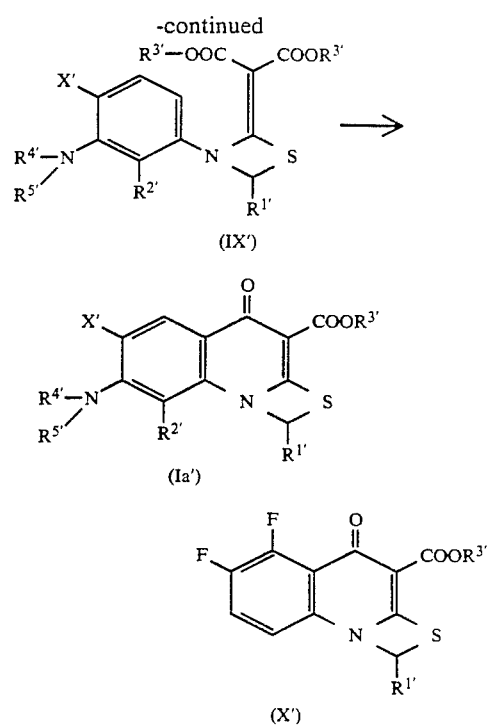

In the formulae, definitions for R¹', R²', R³', R⁴', R⁵' and X' are the same as those in the Method A.

Thus, (VIII') and a dihalide are made to react in the presence of an acid removing agent (e.g. potassium carbonate) in an inert solvent (e.g. N,N-dimethylformamide). Then (IX') is subjected to a ring closure to manufacture (IIa'). This ring closure reaction can be done by a known method known per se such as, for example, a method by heating and a method using acidic substance such as phosphorus oxychloride, phosphorus pentachloride, phosphorus trichloride, thionyl chloride, fuming sulfuric acid, concentrated sulfuric acid, polyphosphoric acid, polyphosphate, etc. When an acidic substance is applied, its amount is 1 mole to large excess (more preferably 20 to 30 molds) of acidic substance to 1 mole of (IX') and the reaction is usually conducted at 0° to 100° C. (more preferably to 0° to 60° C.). It is also possible that a thiazetidine ring is formed starting from 3,4-difluoro substance and then condensed with an amine by the same way as in the Method C to give (IIa'). When R²' is hydrogen, (X') is produced as a side product and, after removing it from the reaction mixture, the residue is made to react with an amine. Or the separation is carried out after the condensation with an amine.

When a diamine such as piperazine is used as a reactant in the above manufacturing methods, one of the amine groups is protected, if necessary, by a known method. The amine is made to react with (VI') and then the protective groups are detached to afford the desired compound (N-nonsubstituted compound). It is also possible that substituent(s) is(are) introduced to the nitrogen atom to the N-nonsubstituted compound by a known method per so to manufacture N-substituted diamino compound.

An 8-substituted derivative can also be manufactured by introduction of desired substituent(s) to the compound obtained hereinabove (where R²' is hydrogen) by a method known per se.

When the compound manufactured by the above methods is an ester (i.e. $R^{3'}$ is alkyl), it may be hydrolyzed, if desired, to give the corresponding carboxylic acid (i.e. $R^{3'}$ is hydrogen). This hydrolysing reaction is conducted by the use of a large excess of acid (e.g. sulfuric acid, fumic sulfuric acid, hydrochloric acid, hydrobromic acid, hydrobromic acid/acetic acid, chlorosulfonic acid, polyphosphoric acid, and the like) and, more preferably 10 to 20 times excess of acid as a solvent, at room temperature to 110° C. Alterna-tively, the hydrolysis may also be conducted by stirring, at room temperature to 60° C., in a 1 to 5% aqueous alcohol (e.g., methanol, ethanol, propanol and butanol; among them, tert-butanol is preferred) of 20 to 30 times excess (preferably 5 to 5 times excess) of potassium hydroxide or sodium hydroxide.

Another method is to heat the ester with stirring at 60°-150° C., preferably at 100° t 110° C., in 10 to 100 times excess of alcohol corresponding to desired ester in the presence of a catalytic amount of concentrated sulfuric acid whereupon the desired ester can be afforded.

A carboxylic acid ($R^{3'}$ is hydrogen), is, if desired, esterified to give an ester (e.g. $R^{3'}$ is alkyl). In this esterification, an esterification method known per se may be used such as, for example, the use of thionyl chloride and alcohol; alcohol and condensing agent (e.g. dicyclocarbodiimide); or alkyl halide and alcoholate. In the case of the carboxylic acid, it may be used in a form pharmacologically-acceptable salt (e.g. sodium or potassium salts) by a known method per se.

Some of the starting compounds (II') and (VIII') are novel and such novel compounds may be manufactured by a known method (e.g. see U.S. Pat. No. 4,661,346) or by the same method as the Reference Examples given later.

Novel starting compounds (VI') are given later in Reference Examples and they are manufactured in the same or similar manner as the above Method A or Method B. The amine ($R^{4'}R^{5'}NH$) is a known substance or can be manufactured in a similar manner to known methods.

The desired compound (II') prepared as such can be separated and purified by various means known per se such as, for example, concentration, conversion of liquid properties, transfer to another solvent, extraction with a solvent, crystallization, recrystallization, fractional distillation, chromatography, and the like.

Compound III can be prepared by halogenating 4,5-dimethyl-2-oxo-1,3-dioxolene of a formula

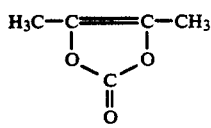

The starting material (V) used here is known and is disclosed, for example, in Bull. Chem. Soc. Japan, vol. 45, pages 2797-2801 (1972); Transactions Illinois State Academic Sci., vol. 67, pages 139-144 (1974); Tetrahedron Letters, 1972, pages 1701-1704; and U.S. Pat. No. 3,020,290.

In the manufacture of the compound (III) in which X' is chlorine or bromine by halogenation of the compound (V), the compound (V) is made to react with equimolar or an excess of chlorine, bromine, N-bromophthalimide, N-bromosuccinimide, N-chlorohthalimide, N-chlorosuccinimide or other chlorinating or brominating agent in inert organic solvent such as methylene chloride, chloroform, carbon tetrachloride, benzene, etc. preferably under a radical-generating condition. The compound (III) in which X' is iodine can be prepared by subjecting the resulting compound as such (i.e. chlorinated one which is (III) wherein X' is chlorine atom; or brominated one which is (III) wherein X' is bromine atom) to a halogen substitution by a conventional means using, for example, potassium iodide.

The prepared compound (I) as such can be isolated and purified by a known per se method such as, for example, concentration, pH conversion, transfer to another solvent, extraction with a solvent, crystallization, recrystallization, fractional distillation, chromatography, etc.

When the compounds of the present invention are administered as pharmaceuticals, to humans and animals, they are given per se or as a pharmaceutical composition containing, for example, 0.1 to 99.5% (more preferably, 0.5 to 90%) of active ingredient in combination with a pharmaceutically acceptable carrier.

The quinolinecarboxylic acid derivatives of the present invention may be given orally, parenterally, topically, or rectally. They are, of course, given by forms suitable for each administration route. For example, they are administered in tablet or capsule form, by injection, inhalation, eye lotion, ointment, suppository, etc. administration by injection, infusion or inhalation; topical by lotion or ointment; and rectal by suppositories. Oral administration is preferred.

As to carriers, one or more liquid, solid or semisolid diluent, filler and other auxillary agents for pharmaceutical preparations may be used. It is desired that the pharmaceutical compositions are administered in unit dosage form.

Oral administration can be effected utilizing solid and liquid dosage unit forms such as powders, tablets, capsules, granules and the like.

Powders are prepared by comminuting the compound to a suitable fine size and mixing with a similarly comminuted pharmaceutical carrier such as an edible carbohydrate as, for example, starch or mannitol. Flavoring, preservative, dispersing and coloring agents can also be present.

Capsules are made by preparing a powder mixture as described above and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder as carboxymethyl cellulose, an alginage, gelatin, or polyvinyl pyrrolidone, a solution retardant such as paraffin, a resorption accelerator such as a quarternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the resulting imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds and pharmaceutically accetable acid addition salts of the present invention can also be combined with free flowing inert carriers and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solutions, syrups and elixirs can be prepared in dosage unit form so that a given quantity contains a predetermined amount of the compound. Syrups can be prepared by dissolving the compound in a suitably flavored aqueous solution, while elixirs are prepared through the use of a nontoxic alcoholic vehicle. Suspensions can be formulated by dispersing the compound in a nontoxic vehicle. Solubilizers and emulsifiers such as ethoxylated isostearyl alcohols and polyoxyethylene sorbitol esters, preservatives, flavor additives such as peppermint oil or saccharin, and the like can also be added.

Where appropriate, dosage unit formulations or oral administration can be microencapsulated. The formulation can also be prepared to prolong or sustain the release as for example by coating or embedding particulate material in polymers, wax or the like.

Parenteral administration can be effected utilizing liquid dosage unit forms such as sterile solutions and suspensions intended for subcutaneous, intramuscular or intravenous injection. These are prepared by suspending or dissolving a measured amount of the compound in a nontoxic liquid vehicle suitable for injection such as aqueous or oleaginous medium and sterilizing the suspension or solution. Alternatively, a measured amount of the compound is placed in a vial and the vial and its contents are sterilized and sealed. An accompanying vial or vehicle can be provided for mixing prior to administration. Nontoxic salts and salt solutions can be added to render the injection isotonic. Stabilizers, preservatives and emulsefiers can also be added.

Rectal administration can be effected utilizing suppositories in which the compound is admixed with low-melting, water-soluble or insoluble solids such as polyethylene glycol, cocoa butter, higher esters as for example flavored aqueous solution, while elixirs are prepared through myristyl palmitate or mixtures thereof.

In determining the dosage for treating bacterial infections a number of factors such as the age of the patient, body weight, severity of condition, administration route, and the like must be considered. Generally, 50 to 1000 mg is administered per day for a human adult preferably 100 to 300 mg per day for a human adult orally. In some cases, a lower dose is sufficient and, in some other cases, a higher dose or more doses may be necessary. The administration may be once a day or divided among administration several times a day.

It is preferred that the administration be divided so that it takes place 2 or 3 times per day.

REFERENCE EXAMPLE 1

Ethyl 6,7-difluoro-1-methyl-4-oxo-4H-(1,3)thiazeto(3,2-a)quinoline-3-carboxylate (1) 3,4-Difluoroaniline (600 g) and 1410 g of triethylamine were mixed and, with ice cooling and stirring, 389 g of carbon disulfide was dropped in during 2.5 hours. The mixture was stirred at the same temperature for 2 hours more whereupon crystals gradually appeared. The mixture was gradually warmed up to the room temperature, stirred for 2 hours, and kept in a refrigerator for two nights. Chloroform (2 liters) was added to the reaction mixture in which crystals were solidified, the mixture was stirred to make it suspended, and ethyl chloroformate was dropped in at 10° C. (inner temperature) during 2 hours. The mixture was stirred 3.5 hours more at room temperature. After the reaction, the reaction solution was poured over into ice water, the mixture was made weekly acidic with concentrated hydrochloric acid, and the chloroform layer was collected. This was washed with water, dried and concentrated and the residue was purified by a column chromatography (n-hexane/silica gel) to give 558.6 g of 3,4-difluorophenyl isothiocyanate in colorless oil.

(2) Ethyl malonate (200.3 g) was dropped into a stirring mixture of 2850 ml of dioxane and finely-powdered potassium hydroxide during 3 hours. After the dropping was completed, 182.6 g of oil obtained in (1) was dropped in at room temperature with stirring and then the mixture was stirred for 18 hours. Methoxymethyl chloride (100.2 g) was gradually dropped in with ice cooling and stirring, then stirred at room temperature for 3 hours, poured over into ice water, extracted with ethyl acetate, and the extract was washed with water and dried. The resulting residue was purified by a silica gel column chromatography n-hexane/ethyl acetate (2:1) was used as an eluting solution) to give 383.8 g of oily diethyl 1-(3,4-difluorophenylamino)-1-(methoxymethylthio)-methylenemalonate.

(3) The oily substance (85.5 g) obtained in the above (2) was dissolved in 250 g of diphenyl ether and the solution was heated with stirring at 240° C. for 5 to 10 minutes. This was cooled to 80° C., poured over into 1 liter of n-hexane, and allowed to stand overnight in a cool place. Crystals separated out therefrom were collected by filtration and washed with n-hexane to give 195 g of ethyl 6,7-difluoro-4-hydroxy-2-methoxymethylthioquinoline-3-carboxylate, pale yellow crystals, m.p. 126°–129° C.

(4) Concentrated hydrochloric acid (600 ml), was dropped into a suspension of 195 g of the crystals obtained in (3) in 1 liter of ethanol at room temperature with stirring. After the dropping was completed, the mixture was stirred for 2 hours, ice water was added thereto, the crystals separated out therefrom were collected by filtration, washed with water and air-dried to give 166.6 g of ethyl 6,7-difluoro-4-hydroxy-2-mercaptoquinoline-3-carboxylate, yellow crystals, m.p. 201°–203° C. (decomposition).

(5) Ethylidene bromide (110.0 g), 77.4 g of potassium carbonate, 4.6 g of potassium iodide and 540 ml of N,N-dimethylformamide were placed in a flask and heated with stirring at 105°–110° C. A solution of 80 g of crystals obtained in (4) in 1400 ml of N,N-dimethylformamide was dropped into the above solution. After the dropping was completed, the mixture was stirred at the same temperature for 2.5 hours. After the reaction was completed, the mixture was concentrated in vacuo. The concentrated solution was poured over into ice water and crystals separated out were collected with filtration followed by washing with water and drying with air to give 61.4 g of ethyl, 6,7-difluoro-1-methyl-4-oxo-4H-(1,3)thiazeto(3,2-a) quinoline-3-carboxylate as crude crystals. This was recrystallized from a 10:1 mixture of chloroform and methanol to give 41.2 g of colorless crystals. Melting point: 200°–202° C.

Elementary analysis calculated for $C_{14}H_{11}F_2NO_3S$. Calcd (%): C 54.02, H 3.56, N 4.50. Found (%): C 54.54, H 3.42, N 4.29.

REFERENCE EXAMPLE 2

(1) 2-Fluoro-6-methoxyaniline (7.80 g) and 17.23 g of di-(2-bromoethyl)amine hydrobromide were dissolved in 5 ml of water and, by heating at about 110° C. on a bath, 10 ml of 30% potassium hydroxide solution was added thereto (each about 3.5 ml once an hour). Heating was further continued (7 hours in total). After cooled, the reaction solution was made alkaline with aqueous solution of sodium hydroxide to salt out and extracted with chloroform twice. The extract was washed with saturated sodium chloride solution, dried over sodium sulfate, the solvent was evaporated therefrom, and the residue was purified by a column chromatography to give 8.95 g of oily 1-(2-fluoro-6-methoxyphenyl)piperazine in 34.93 g yield or 94%.

(2) The compound (34.89 g) obtained by the same manner as in the above (1) was dissolved in 50 g of formic acid and 135 g of 37% formaline and the solution was heated to reflux for 75 minutes at the bath temperature of 110° C. The reaction solution was concentrated in vacuo and dissolved in diluted hydrochloric acid. Insoluble matters were removed, the residue was washed with ethyl acetate, made alkaline with aqueous solution of sodium hydroxide, salted out, and extracted with chloroform. The extract was dried over sodium sulfate and the solvent was evaporated therefrom. The residue was dissolved in ether, hydrochloric acid/ethanol was added thereto, and the hydrochloride was separated out therefrom. The crystals were washed with ether, dried, dissolved in water, sodium hydroxide solution was added, and extracted with ether. The extract was washed with saturated sodium chloride solution, dried over sodium sulfate, and the solvent was evaporated therefrom to give 26.18 g of oily 1-(2-fluoro-6-methoxyphenyl)-4-methylpiperazine, yield 70%.

(3) The compound (27.56) obtained by the same manner as in the above (2) and 42.14 g of silver sulfate were dissolved in 600 ml of concentrated sulfuric acid, a solution of 21.60 g of bromine in 1200 ml of concentrated sulfuric acid was dropped therein during about 30 minutes with ice-cooling, and the stirring was continued for another 90 minutes. The reaction solution was poured over into ice, the mixture was made alkaline with sodium hydroxide with ice cooling, and extracted with chloroform twice. The extract was washed with saturated sodium chloride solution and dried over sodium sulfate. The solvent was evaporated therefrom and purified by a column chromatography to give 14.12 g of 1-(3-bromo-2-fluoro-6-methoxyphenyl)-4-methylpiperazine. Yield 38%.

(4) The compound (13.42 g) obtained by the same manner as in the above (3) was dissolved in 500 ml of concentrated sulfuric acid and a solution of 4.70 g of potassium nitrate in 70 ml of concentrated sulfuric acid was dropped in during 20 minutes with ice-cooling (temperature being 4° to 6° C.). This was stirred for 30 minutes more, then poured over into ice water, the mixture was made weakly alkaline with sodium bicarbonate, and extracted with ethyl acetate. The extract was washed with saturated sodium chloride solution and dried over sodium sulfate. The solvent was evaporated therefrom and purified with a column chromatography to give 3.29 g of 1-(3-bromo-2-fluoro-5-nitro-6-methoxyphenyl)-4-methylpiperazine. Yield 21%.

(5) The compound (2.778 g) obtained by the same manner as into the above (4) was dissolved in 60 ml of concentrated hydrochloric acid and a solution of 7.38 g of stannous chloride dihydrate in 80 ml of concentrated hydrochloric acid was dropped in with ice-cooling. After completion of the dropping, the mixture was stirred for 30 minutes more, poured over into ice, neutralized with diluted sodium hydroxide, and extracted with chloroform. The extract was washed with saturated sodium bicarbonate solution, dried over sodium sulfate, and the solvent was evaporated therefrom in vacuo. As a residue was obtained 2.432 g of 1-(5-amino-3-bromo-2-fluoro-6-methoxyphenyl)-4-methylpiperazine. Yield 96%.

(6) The compound (2.33 g) obtained by the same manner as in the above (5) was dissolved in 150 ml of ethanol, then 0.30 g of sodium hydroxide and 200 mg of 5% palladium-carbon were added, and the catalytic reduction was conducted at room temperature and ordinary pressure. The reaction solution was filtered and the filtrate was concentrated in vacuo. This was extracted with chloroform, the extract was washed with saturated sodium bicarbonate solution, dried over sodium sulfate and the solvent was evaporated therefrom to give 1.68 g of 1-(5-amino-2-fluoro-6-methoxyphenyl)-4-methylpiperazine.

The following nonlimitative examples more particularly illustrate the present invention:

EXAMPLE 1

Ethyl 6-fluoro-1-methyl-7-[4-(5-methyl-2-oxo-1,3-dioxolen-4yl)methyl-1-piperazinyl]-4oxo-4H-[1,3-]thiazeto[3,2-a]quinoline-3-carboxylate.

Ethyl 6-fluoro-1-methyl-4-oxo-7-(1-piperazinyl)-4H-[1,3]thiazeto[3,2-a]quinoline-3-carboxylate (3.88 g) and 1.23 g of potassium bicarbonate were suspended in 20 ml of N,N-dimethylformamide, 2.38 g of 4-bromomethyl-5-methyl-1,3-dioxolen-2-one was dropped thereinto with ice cooling, and the mixture was stirred for 3 hours. After the reaction, the solvent was evaporated in vacuo therefrom at 50° C. and the residue was extracted with chloroform containing a few amount of methanol. The extract was washed with water, dried, the solvent was evaporated therefrom and the residue was purified by a column chromatography (chloroform-methanol/silica gel) to give 3.32 g of desired product. M.p. 241°–243° C. (decompn.)

Elem. Anal. for $C_{23}H_{24}FN_3O_6S$; Calcd. (%) C: 56.43 H: 4.94 N: 8.58; Found (%) C: 56.13 H: 4.99 N: 8.26.

I R (KBr) $\nu$ (cm$^{-1}$): 1820, 1720 (carbon-yl).

N M R (CF$_3$CO$_2$D)(ppm) 1.51(3H, COOCH$_2$CH$_3$, t), 2.31(3H, s), 2.35(3H,

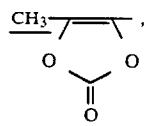

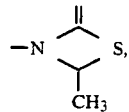

d), 3.40~4.30(8H, proton in piperazine ring, m), 4.55(2H,

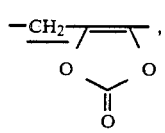

s), 4.65(2H, COOCH₂CH₃, q), 6.51(1H,

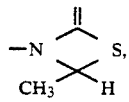

q), 7.05(1H, 8-proton, d), 8.11(1H, 5-proton, d).

EXAMPLE 2

6Fluoro-1-methyl-7-([4-(5-methyl-2-oxo-1,3-dioxolen-4-yl)methyl-1-piperazinyl]-4-oxo-4H-[1,3]thiazeto[3,2-a]quinoline-3-carboxylic acid.

6-Fluoro-1-methyl-4-oxo-7-(1-piperazinyl)-4H-[1,3]thiazeto[3,2-a]quinoline-3-carboxylic acid (2.5 g) and 1.52 g of potassium bicarbonate were suspended in 40 ml of N,N-dimethylformamide, 1.52 g of 4-bromomethyl-5methyl-1,3-dioxolen-2-one was dropped thereinto with ice cooling, and the mixture was stirred for 3 hours. After the reaction, the mixture was evaporated in vacuo at 60° C., the residue was poured over into ice water, insoluble substance was collected by filtration, washed with water, air-dried, the resulting crude crystals were recrystallized from chloroform-methanol (10:1), and 2.05 g of the desired product was obtained. M.p. 138°-140° C. (decompn.).

Elem. Anal. for $C_{21}H_{20}FN_3O_6S.1\frac{1}{2}H_2O$: Calcd. (%) C: 51.32 H: 4.79 N: 8.55; Found (%) C: 51.39 H: 4.94 N: 8.30.

I R (KBr) ν (cm⁻¹): 1815, 1700. N M R (CF₃CO₂D)(ppm) 2.31(3H,

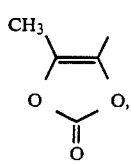

t), 2.35(3H,

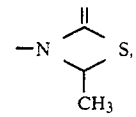

d), 3.40~4.30(8H, proton in piperazine ring, m), 4.55(2H,

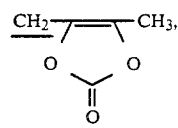

s), 6.55(1H,

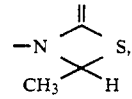

q), 7.05(1H, 8-proton, d), 8.15(1H, 5-proton, d)

EXAMPLE 3

6-Fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid hydrochloride.

The compound (500 mg) prepared in Example 2 was dissolved in chloroform and 0.5 ml of 33% methanolic hydrochloric acid was added thereto. The crystals separated out therefrom were collected by filtration, washed with small amount of methanol and then with ether, and dried in vacuo to give 470 mg of desired product, m.p. 234°-237° C. (decompn.).

Elem. Anal. for $C_{21}H_{20}FN_3O_6S.HCl.2H_2O$; Calcd (%) C: 47.24 H: 4.72 N: 7.87; Found (%) C: 47.54 H: 4.59 N: 7.77.

EXAMPLE 4

6-Fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid methanesulfonate Similarly prepared was the title product by the same manner as in Example 3. M.p. 230°-233° C. (decompn.).

Elem. Anal. for $C_{21}H_{20}FN_3O_6S.CH_3SO_3H.1\frac{1}{2}H_2O$. Calcd (%): C: 45.20 H: 4.66 N: 7.19; Found (%): C: 45.14 H: 4.50 N: 7.01.

EXAMPLE 5

6-Fluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylic acid.

6-Fluoro-4-oxo-1-phenyl-7-(1-piperazinyl)-4H-[1,3]-thiazeto-[3,2-a]quinoline-3-carboxylic acid (3.0 g) and 0.88 g of potassium bicarbonate were suspended in 50 ml of N,N-dimethylformamide, 1.69 g of 4-bromomethyl-5-methyl-1,3-dioxolen-2-one was dropped thereinto with ice cooling, and the mixture was stirred for 3 hours. After the reaction, the mixture was poured into ice water, the crystals separated out therefrom was collected by filtration, washed with water, dried in vacuo, and the resulting crude crystals were recrystallized from chloroform-ethanol to give 1.3 g of desired product, m.p.201°-202° C. (decompn.).

Elem. Anal. for $C_{26}H_{22}FN_3O_6S \cdot \frac{1}{2}H_2O$: Calcd. (%) C: 58.15 H: 4.41 N: 7.82; Found (%) C: 58.10 H: 4.31 N: 7.80.

I R (KBr) $\nu$ (cm$^{-1}$): 1810, 1710

N M R (CF$_3$CO$_2$D)(ppm) 2.25(3H,

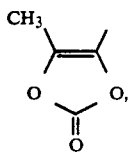

s), 3.00~4.30(8H, proton in piperazine ring, m), 4.42(2H,

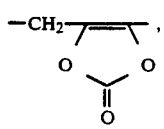

s), 6.43(1H, 8-proton, d), 7.25(1H,

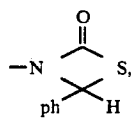

s), 7.53(5H, ph, s), 8.08(1H, 5-proton, d)

EXAMPLE 6

Ethyl 6-fluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylate)

Ethyl 6-fluoro-4-oxo-1-phenyl-7-(1-piperazinyl)-4H-[1,3]thiazeto[3,2-a]quinoline-3-carboxylate (3.0 g) and 0.82 g of potasium bicarbonate were suspended in 50 ml of N,N-dimethylformamide, 1.58 g of 4-bromomethyl-5-methyl-1,3-dioxolen-2-one was dropped thereinto with ice cooling, and the mixture was stirred for 3 hours. After the reaction, the mixture was poured over into ice water and the crystals separated out therefrom were collected by filtration. They were then dissolved in chloroform, the solution was washed with water, and evaporated/dried in vacuo. The resulting oily residue was purified by a column chromatography (silica gel/-methanolchloroform [1:50]) to give 2.47 g of desired product, mp, 223°–226° C. (decompn.).

Elem. Anal. for $C_{28}H_{26}FN_3O_6S \cdot \frac{1}{2}H_2O$; Calcd. (%) C:59.99 H: 4.85 N: 7.50; Found (%) C: 60.10 H: 5.04 N: 7.34.

N M R (CF$_3$CO$_2$D)(ppm) 1.54(3H, COOCH$_2$CH$_3$, t), 2.25(3H,

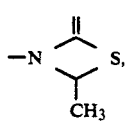

d), 2.28(3H, —CH$_3$, s), 3.10~4.20(8H, proton in piperazine ring, m), 4.47(2H,

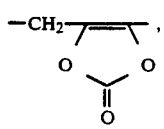

s), 4.65(2H, COOCH$_2$—CH$_3$, q) 6.45(1H, 8-proton, d) 7.28(1H,

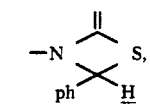

s), 7.55(5H, ph, s), 8.10(1H, 5-proton, d).

Similarly prepared were the following compounds.

EXAMPLE 7

6,8-Difluoro-7-[4-(5-methyl-2-oxo-1,3-dioxolen-4-yl)methyl-1-piperazinyl]-4-oxo-4H-[1,3]thiazeto[3,2-a]quinoline-3-carboxylic acid.

M.p. 255° C. (decompn.)

Elem Anal. for $C_{20}H_{17}H_2N_3O_6S$: Calcd (%) C; 51.61 H: 3.68 N: 9.03; Found (%) C: 51.92 H: 3.85 N: 8.57.

Mass analysis ($C_{20}H_{17}H_2N_3O_6S$), M$^+$: 465.

EXAMPLE 8

6,8-Difluoro-1-methyl-7-[4-(5-methyl-2-oxo-1,3-dioxolen-4-yl)methyl-1-piperazinyl]-4-oxo-4-[1,3]-thiazeto[3,2-a]quinoline-3-carboxylic acid.

M.p. 168°–171° C.

Elem. Anal. for $C_{21}H_{19}F_2N_3O_6S \cdot \frac{1}{2}H_2O$: Calcd (%) C: 51.63 H: 3.14 N: 8.60; Found (%) C: 51.47 H: 3.92 N: 8.46.

Mass analysis ($C_{21}H_{19}F_2S_6O$), M$^+$: 479.

EXAMPLE 9

6,8-Difluoro-7-[4-(5-methyl-2-oxo-1,3-dioxolen-4-yl)methyl-1-piperazinyl]-4-oxo-1-phenyl-4H-[1,3]-thiazeto[3,2-a]quinoline-3-carboxylic acid.

M.p. 160°–161° C. (decompn.)

Elem. Anal. for $C_{26}H_{21}F_2N_3O_6S$: Calcd (%) C: 57.61 H: 3.91 N: 7.76; Found (%) C: 57.26 H: 3.97 N: 7.64.

Mass analysis ($C_{26}H_{21}F_2N_3O_6S$), M$^+$: 541.

EXAMPLE 10

6,8-Difluoro-1-(4-fluorophenyl)-7-[4-(5-methyl-2-oxo-1,3-dioxolen-4-yl)methyl-1-piperazinyl]-4-oxo-4H-[1,3]-thiazeto[3,2-a]quinoline-3-carboxylic acid.

Mass analysis ($C_{26}H_{20}F_3N_3O_6S$), M$^+$: 559.

EXAMPLE 11

6,8-Difluoro-1-(2,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid.

Mass analysis ($C_{26}H_{19}F_4N_3O_6S$), M$^+$: 577.

EXAMPLE 12

6,8-Difluoro-1-(3,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid.

Mass analysis ($C_{26}H_{19}F_4N_3O_6S$), M$^+$: 577.

EXAMPLE 13

6-Fluoro-8-methoxy-7-[4-(5-methyl-2-oxo-1,3-dioxolen-4-yl)methyl-1-piperazinyl]-4-oxo-4H-[1,3]thiazeto[3,2-a]quinoline-3-carboxylic acid.

Mass analysis $C_{21}H_{20}FN_3O_7S$), M+: 515.

EXAMPLE 14

6-Fluoro-8-methoxy-1-methyl-7-[4-(5-methyl-2-oxo-1,3-dioxolen-4-yl)methyl-1-piperazinyl]-4-oxo-4H-[1,3]-thiazeto[3,2-a]quinoline-3-carboxylic acid.

M.p. 158°–159° C.

Elem. Anal. for $C_{22}H_{22}FN_3O_7S$: Calcd (%) C: 53.76 H: 4.51 N: 8.55; Found (%) C: 53.47 H: 4.64 N: 8.69.

Mass analysis ($C_{22}H_{22}FN_3O_7S$), M+: 529.

EXAMPLE 15

6-Fluoro-8-methoxy-7-[4-(5-methyl-2-oxo-1,3-dioxolen-4yl)methyl-1-piperazinyl]-4-oxo-4H-[1,3]thiazeto[3,2-]quinoline-3-carboxylic acid.

Mass analysis ($C_{27}H_{24}FN_3O_7S$), M+: 591.

DATA

The result of a pharmacological test showing the usefulness of the representative compounds of the present invention is given below.

1. Measurement of minimum growth-inhibition concentrations (MIC).

Test Method: In accordance with a standard method by Japan Chemotherapeutic Society [Chemotherapy, 29(1), pages 76–79, 1981], agar plate dilution method was used and the MIC was measured. Thus, bouillon for measuring sensitivity was used and the bacterial liquid cultured at 37° C. for 18 hours was diluted to an extent of $10^6$ CFU/ml using said medium. This was inoculated to an agar medium containing drug for measuring sensitivity using a microplanter, cultured at 37° C. for 18 hours, and MIC was measured. Ofloxacin was used for comparison/control. The result is given in Table 1. It is apparent that the present invention compounds exhibit strong antibacterial activity against *Pseudomonas aeruginosa* and both gram-positive and negative bactera.

TABLE 1

|  | MIC (μg/ml) | |
| --- | --- | --- |
|  | The Present Invention Compd. | Comparison/Control |
| *Staphylococcus aureus* 209-P JC-1 | 0.1 | 0.39 |
| *Streptococcus pyogenes* S-23 | 0.39 | 1.56 |
| *Streptococcus pneumoniae* Type I | 0.39 | 1.56 |
| *Bacillus subtilis* ATCC 6633 | 0.05 | 0.1 |
| *Escherichia coli* N1JH JC-2 | 0.0125 | 0.1 |
| *Klebsiella pneumoniae* NCTC 9632 | 0.0125 | 0.05 |
| *Serratia marcescens* IFO 3736 | 0.2 | 0.78 |
| *Proteus mirabilis* IFO 3849 | 0.025 | 0.39 |
| *Shigella flexneri* 2a EW-10 | 0.0125 | 0.025 |
| *Pseudomonas aeruginosa* IFO 3445 | 0.2 | 1.56 |

The compound of Example 2 was used as representative of the compounds of the present invention and ofloxacin was used as the Comparison/Control.

2. Therapeutic effect on infection in mice.

Test method: *E. coli* KC-14 and *P. aeruginosa* E-2 were suspended in 5% mucin and 0.5 ml of the suspension was injected intraperitoneally to ddY strain male mice (body weight: ca. 20 g; four weeks age; 10 mice per group). The amount of the bacteria inoculated was $5.1 \times 10^4$ CFU/mouse for *E. coli* and $7.5 \times 10^4$ CFU/mouse for *P. aeruginosa*. The drug was given orally once after 2 hours of inoculation and, out of the survival rate after one week, an $ED_{50}$ was calculated by a Probit method. Ofloxacin was used as the comparison/control. The results are given in Table 2.

TABLE 2

| Compound Tested (Example Number) | $ED_{50}$ (mg/mouse) E. Coli | P. aeruginosa |
| --- | --- | --- |
| 1 | — | 0.354 |
| 2 | 0.0078 | 0.154 |
| 3 | 0.0078 | 0.125 |
| 4 | 0.0078 | 0.125 |
| 8 | 0.0078 | 0.125 |
| 14 | 0.0152 | 0.427 |
| Ofloxacin | 0.011 | 0.692 |

It is apparent that the compounds of the present invention exhibit strong antibacterial effect to infectious bacterial diseases in mice.

From the above facts and results it is clear that the compounds of the present invention are effective at far lower doses than the conventional antibacterial agents not only against *P. aeruginosa* but also against both gram-positive and negative bacteria. They exhibit a wide antibacterial spectrum.

Moreover, their absorption after oral administration is better than the conventional drugs whereupon they are converted to active form promptly showing good therapeutic effect.

Furthermore, the compounds of the present invention have very low toxicity and, accordingly, they can be administered with high safety, as therapeutic agents to treat systemic infectious diseases and topical ones such as infectious diseases in the urinary gall tracts of mammals including humans.

What is claimed is:

1. A compound of the formula (I)

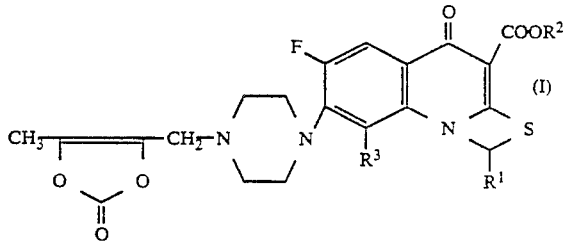

or a pharmaceutically acceptable salt thereof wherein $R^1$ is hydrogen, straight or branch chain lower alkyl or phenyl unsubstituted or substituted by one or two halo moieties; $R^2$ is hydrogen or straight or branch chain lower alkyl; and $R^3$ is hydrogen, halo or straight or branch chain lower alkoxy.

2. A compound according to claim 1 wherein $R^1$ is hydrogen, straight or branch chain alkyl of 1 to 4 carbon atoms, phenyl or halophenyl.

3. A compound according to claim 1 wherein $R^2$ is hydrogen or straight or branch chain alkyl of 1 to 4 carbon atoms.

4. A compound according to claim 1 wherein $R^3$ is hydrogen, halo or straight or branch chain alkoxy of 1 to 4 carbon atoms.

5. A compound according to claim 1 wherein $R^1$ is hydrogen, straight or branch chain alkyl of 1 to 4 carbon atoms, phenyl or halophenyl; $R^2$ is hydrogen or straight or branch chain alkyl of 1 to 4 carbon atoms; and R³ is hydrogen, halo or straight or branch chain alkoxy of 1 to 4 carbon atoms.

6. A compound according to claim 1 wherein R¹ is hydrogen, straight or branch chain alkyl of 1 to 4 carbon atoms, phenyl or fluorophenyl; R² is hydrogen or straight or branch chain alkyl of 1 to 4 carbon atoms; and R³ is hydrogen, fluoro or straight or branch chain alkoxy of 1 to 4 carbon atoms.

7. A compound according to claim 1 in the form of a pharmaceutically acceptable salt.

8. The compound according to claim 1 which is ethyl 6-fluoro-1-methyl-7-[4-(5-methyl-2-oxo-1,3-dioxolen-4-yl)methyl-1-piperazinyl]-4-oxo-4H-[1,3-]thiazeto[3,2-a]quinoline-3-carboxylate, 6-fluoro-1-methyl-7-([4-(5-methyl-2-oxo-1,3-dioxolen-4-yl)methyl-1-piperazinyl]-4-oxo-4H-[1,3]thiazeto[3,2-a]quinoline-3-carboxylic acid, 6-fluoro-1-methyl-7-[4-(5-methyl-2-oxo-1,3-dioxolen-4-yl)methyl-1-piperazinyl]-4-4H-[1,3]thiazeto[3,2-a]quinoline-3-carboxylic acid hydrochloride, 6-fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid methanesulfonate, 6-fluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylic acid, ethyl 6-fluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylate, 6,8-difluoro-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylic acid, 6,8-difluoro-1-(4-fluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-(2,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-(3,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6-fluoro-8-methoxy-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6-fluoro-8-methoxy-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid or 6-fluoro-8-methoxy-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylic acid.

9. A pharmaceutical composition useful for treating bacterial infections in humans and animals which comprises an antibacterially effective amount of a compound of the formula (I)

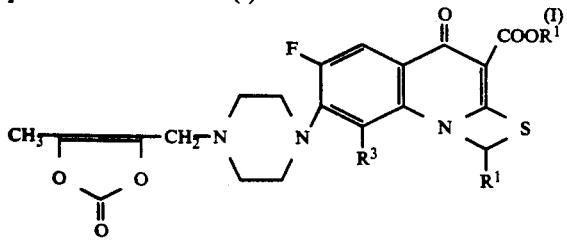

or a pharmaceutically acceptable salt thereof wherein R¹ is hydrogen, straight or branch chain lower alkyl or phenyl unsubstituted or substituted by one or two halo moieties; R² is hydrogen or straight or branch chain lower alkyl; and R³ is hydrogen, halo or straight or branch chain lower alkoxy, in combination of the pharmaceutically acceptable carrier.

10. A composition according to claim 9 wherein R¹ is hydrogen, straight or branch chain alkyl of 1 to 4 carbon atoms, phenyl or halophenyl.

11. A composition according to claim 9 wherein R² is hydrogen or straight or branch chain alkyl of 1 to 4 carbon atoms.

12. A composition according to claim 9 wherein R³ is hydrogen, halo or straight or branch chain alkoxy of 1 to 4 carbon atoms.

13. A composition according to claim 9 wherein R¹ is hydrogen, straight or branch chain alkyl of 1 to 4 carbon atoms, phenyl or halophenyl; R² is hydrogen or straight or branch chain alkyl of 1 to 4 carbon atoms; and R³ is hydrogen, halo or straight or branch chain alkoxy of 1 to 4 carbon atoms.

14. A composition according to claim 9 wherein R¹ is hydrogen, straight or branch chain alkyl of 1 to 4 carbon atoms, phenyl or fluorophenyl; R² is hydrogen or straight or branch chain alkyl of 1 to 4 carbon atoms; and R³ is hydrogen, fluoro or straight or branch chain alkoxy of 1 to 4 carbon atoms.

15. A composition according to claim 9 wherein the compound is in the form of a pharmaceutically acceptable salt.

16. A composition according to claim 9 wherein the compound is ethyl 6-fluoro-1-methyl-7-[4-(5-methyl-2-oxo-1,3-dioxolen-4-yl)methyl-1-piperazinyl]-4-oxo-4H-[1,3-]thiazeto[3,2-a]quinoline-3-carboxylate,6-fluoro-1-methyl-7-([4-(5-methyl-2-oxo-1,3-dioxolen-4-yl)methyl-1-piperazinyl]-4-oxo-4H-[1,3]thiazeto[3,2-a]quinoline-3carboxylic acid, 6-fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid hydrochloride, 6-fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid methanesulfonate,6-fluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylic acid, ethyl 6-fluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylate, 6,8-difluoro-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-7-[4-(5-methyl-2-oxo-1,3-dioxolen-4-yl)methyl-1-piperazinyl]-4-oxo-1-phenyl-4H-[1,3]-thiazeto[3,2-a]quinoline-3-carboxylic acid, 6,8-difluoro-1-(4-fluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-(2,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-(3,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6-fluoro-8-methoxy-7-[4-(5-methyl-2-oxo-1,3-dioxolen-4-yl)methyl-1-piperazinyl]-4-oxo-4H-[1,3]thiazeto[3,2-a]quinoline-3- carboxylic acid, 6-fluoro-8-methoxy-1-methyl-7-[4-(5-methyl-2-oxo-1,3-dioxolen-4-yl)methyl-1-piperazinyl]-4-oxo-4H-[1,3]-[1,3]thiazeto[3,2-a]quinoline-3-carboxylic acid or 6-fluoro-8-methoxy-7-[4-(5-methyl-2-oxo-1,3-dioxolen-4-yl)methyl-1-piperazinyl]-4-oxo 4H-[1,3]thiazeto[3,2-a]quinoline-3-carboxylic acid.

17. A method of treating bacterial infections in humans and animals which comprises administering to human or animal in need thereof an antibacterially effective amount of a compound of the formula (I)

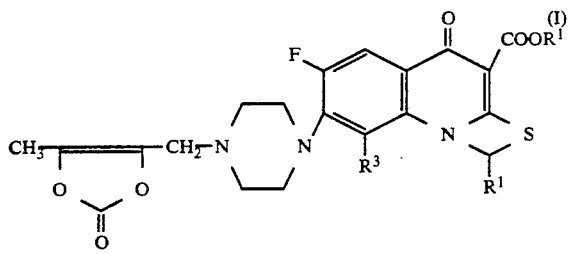

or a pharmaceutically acceptable salt thereof wherein $R^1$ is hydrogen, straight or branch chain lower alkyl or phenyl unsubstituted or substituted by one or two halo moieties; $R^2$ is hydrogen or straight or branch chain lower alkyl; and $R^3$ is hydrogen, halo or straight or branch chain lower alkoxy, in combination of the pharmaceutically acceptable carrier.

18. A method according to claim 17 wherein $R^1$ is hydrogen, straight or branch chain alkyl of 1 to 4 carbon atoms, phenyl or halophenyl.

19. A method according to claim 17 wherein $R^2$ is hydrogen or straight or branch chain alkyl of 1 to 4 carbon atoms.

20. A method according to claim 17 wherein $R^3$ is hydrogen, halo or straight or branch chain alkoxy of 1 to 4 carbon atoms.

21. A method according to claim 17 wherein $R^1$ is hydrogen, straight or branch chain alkyl of 1 to 4 carbon atoms, phenyl or halophenyl; $R^2$ is hydrogen or straight or branch chain alkyl of 1 to 4 carbon atoms; and $R^3$ is hydrogen, halo or straight or branch chain alkoxy of 1 to 4 carbon atoms.

22. A method according to claim 17 wherein $R^1$ is hydrogen, straight or branch chain alkyl of 1 to 4 carbon atoms, phenyl or fluorophenyl; $R^2$ is hydrogen or straight or branch chain alkyl of 1 to 4 carbon atoms; and $R^3$ is hydrogen, fluoro or straight or branch chain alkoxy of 1 to 4 carbon atoms.

23. A method according to claim 17 wherein the compound is in the form of a pharmaceutically acceptable salt.

24. A method according to claim 17 wherein the compound is ethyl 6-fluoro-1-methyl-7-[4-(5-methyl-2-oxo-1,3-dioxolen-4-yl)methyl-1-piperazinyl]-4-oxo-4H-[1,3-]thiazeto[3,2-a]quinoline-3-carboxylate ,6-fluoro-1-methyl-7-([4-(5-methyl-2-oxo-1,3-dioxolen-4-yl)methyl-1-piperazinyl]-4-oxo-4H-[1,3]thiazeto[3,2-a]quinoline-3-carboxylic acid, 6-fluoro-1-methyl-7-[4-(5-methyl- 2-oxo-1,3-dioxolen-4-yl)methyl-1-piperazinyl]-4-oxo-4H-[1,3]thiazeto[3,2-a]quinoline-3-carboxylic acid hydrochloride, 6-fluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid methanesulfonate,6-fluoro-7-[4-(5-methyl-2-oxo-1,3-dioxolen-4 -yl) methyl-1-piperazinyl]-4 -oxo-1-phenyl-4H-[1,3]thiazeto[3,2-a]quinoline-3-carboxylic acid, ethyl 6-fluoro-7-[4-(5-methyl-2-oxo-1,3 dioxolen-4-yl)methyl-1-piperazinyl]-4-oxo-1-phenyl-4H-[1,3]thiazeto[3,2-a]quinoline-3-carboxylate, 6,8-difluoro-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-methyl-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylic acid, 6,8-difluoro-1-(4-fluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-(2,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6,8-difluoro-1-(3,4-difluorophenyl)-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6-fluoro-8-methoxy-7-[4-(5-methyl-2-oxo-1,3-dioxolen-4-yl)methyl-1-piperazinyl]-4-oxo-4H-[1,3]thiazeto[3,2-a]quinoline-3-carboxylic acid, 6-fluoro-8-methoxy-1-methyl-7-[4-(5-methyl-2-oxo-1,3-dioxolen-4-yl)methyl-1-piperazinyl]-4-oxo-4H-[1,3]-thiazeto[3,2-a]quinoline-3-carboxylic acid or 6-fluoro-8-methoxy-7-[4-(5-methyl-2-oxo-1,3-dioxolen-4-yl)methyl-1-piperazinyl]-4-oxo-1-phenyl-4H-[1,3]thiazeto[3,2-a]quinoline-3-carboxylic acid.

* * * * *